United States Patent
Higuchi et al.

(10) Patent No.: US 10,983,319 B2
(45) Date of Patent: Apr. 20, 2021

(54) SURGICAL MICROSCOPE DEVICE AND SURGICAL MICROSCOPE SYSTEM

(71) Applicant: SONY OLYMPUS MEDICAL SOLUTIONS INC., Tokyo (JP)

(72) Inventors: Gakuji Higuchi, Tokyo (JP); Junichi Nozawa, Kanagawa (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 15/567,211

(22) PCT Filed: Mar. 9, 2016

(86) PCT No.: PCT/JP2016/057476
§ 371 (c)(1),
(2) Date: Oct. 17, 2017

(87) PCT Pub. No.: WO2016/181696
PCT Pub. Date: Nov. 17, 2016

(65) Prior Publication Data
US 2018/0106991 A1    Apr. 19, 2018

(30) Foreign Application Priority Data
May 14, 2015  (JP) .............................. JP2015-098679

(51) Int. Cl.
*G02B 21/00* (2006.01)
*G02B 21/24* (2006.01)
(Continued)

(52) U.S. Cl.
CPC .......... *G02B 21/0012* (2013.01); *A61B 90/20* (2016.02); *A61B 90/25* (2016.02);
(Continued)

(58) Field of Classification Search
CPC .......................... G02B 21/00; G02B 21/0004; G02B 21/0012; G02B 21/18; G02B 21/24;
(Continued)

(56) References Cited

U.S. PATENT DOCUMENTS 5,061,018 A * 10/1991 Pederson ............... F16M 13/02
312/209
5,825,536 A * 10/1998 Yasunaga ............... A61B 90/25
359/384

(Continued)

FOREIGN PATENT DOCUMENTS

DE   10 2007 054 450 A1   5/2008
EP       0 781 529 A1    7/1997
(Continued)

OTHER PUBLICATIONS

International Search Report dated Jun. 7, 2016, in PCT;JP2016/057476 filed Mar. 9, 2016.
(Continued)

*Primary Examiner* — Derek S. Chapel
*Assistant Examiner* — Adam W Booher
(74) *Attorney, Agent, or Firm* — Xsensus LLP

(57) ABSTRACT

To enable observation of the operating site to be continued more easily in the case in which the picture of the operating site is no longer displayed normally.
Provided is a surgical microscope device including: a microscope unit that images an observation target, and outputs a picture signal; a support unit that supports the microscope unit, and is configured as a balance arm; and an auxiliary observation device that is attachable to the microscope unit or the support unit, and is configured to enable observation of an observation range provided by the microscope unit.

14 Claims, 9 Drawing Sheets

(51) Int. Cl.
| | |
|---|---|
| *A61B 90/20* | (2016.01) |
| *G02B 23/18* | (2006.01) |
| *G02B 7/00* | (2021.01) |
| *A61B 90/25* | (2016.01) |
| *A61B 90/00* | (2016.01) |
| *A61B 90/50* | (2016.01) |
| *G02B 21/36* | (2006.01) |

(52) U.S. Cl.
CPC ............ *A61B 90/361* (2016.02); *G02B 7/001* (2013.01); *G02B 21/24* (2013.01); *G02B 23/18* (2013.01); *A61B 90/50* (2016.02); *A61B 2090/0818* (2016.02); *G02B 21/242* (2013.01); *G02B 21/244* (2013.01); *G02B 21/368* (2013.01)

(58) Field of Classification Search
CPC .. G02B 21/241; G02B 21/242; G02B 21/244; G02B 21/245; G02B 21/36; G02B 21/361; G02B 21/362; G02B 21/368; A61B 90/20; A61B 90/25; A61B 90/361; A61B 90/37; A61B 90/50; A61B 2090/371; A61B 2090/5025; A61B 2090/504

See application file for complete search history.

(56) References Cited

U.S. PATENT DOCUMENTS

| | | | |
|---|---|---|---|
| 6,050,530 A | | 4/2000 | Nakamura |
| 6,525,878 B1* | | 2/2003 | Takahashi .......... G02B 27/0176 359/466 |
| 8,200,073 B1 | | 6/2012 | Nakamura |
| 2006/0100642 A1* | | 5/2006 | Yang ...................... G06F 3/013 606/130 |
| 2009/0109524 A1* | | 4/2009 | Sander .................... A61B 3/13 359/376 |
| 2009/0190209 A1* | | 7/2009 | Nakamura .......... G02B 21/0012 359/375 |
| 2013/0222897 A1 | | 8/2013 | Yamazaki |
| 2014/0293408 A1 | | 10/2014 | Nakamura et al. |
| 2018/0168769 A1* | | 6/2018 | Wood ................ A61B 1/00188 |

FOREIGN PATENT DOCUMENTS

| | | |
|---|---|---|
| EP | 1 972 294 A1 | 9/2008 |
| EP | 2 044 902 A1 | 4/2009 |
| JP | 8-266555 A | 10/1996 |
| JP | 9-182759 A | 7/1997 |
| JP | 2001-161628 A | 6/2001 |
| JP | 2003-325543 A | 11/2003 |
| JP | 2004-226826 A | 8/2004 |
| JP | 2005-6960 A | 1/2005 |
| WO | WO 2015/042460 A1 | 3/2015 |

OTHER PUBLICATIONS

Extended European Search Report dated Dec. 19, 2018 in European Patent Application No. 16792421.6, citing documents AA, AB, AC, and AO through AS therein, 11 pages.

Notification of Reasons for Refusal dated Nov. 12, 2019, issued in corresponding Japanese Japanese Application No. 2017-517630, 15 pages (with English Translation).

Office Action dated Nov. 1, 2019, issued in corresponding Chinese Patent Application No. 2016800257272, with English Translation, 16 pages.

* cited by examiner

SURGICAL MICROSCOPE DEVICE AND SURGICAL MICROSCOPE SYSTEM

TECHNICAL FIELD

The present disclosure relates to a surgical microscope device and a surgical microscope system.

BACKGROUND ART

In the related art, in surgical operations targeting a fine region, such as neurosurgery, for example, a microscope device for enlarged observation of the operating site is used. The microscope device is made up of a microscope unit supported by an arm unit (support unit) (see Patent Literature 1 and 2, for example).

Since the operating site may be an extremely small region, there is demand for the microscope device to be capable of precisely adjusting the position of the microscope unit to observe a position desired by the surgeon. Consequently, as exemplified by the microscope devices described in Patent Literature 1 and 2, the support unit that supports the microscope unit in many cases is configured as a balance arm that includes a counter weight (counter balance). By configuring the support unit as a balance arm, the surgeon is able to move the microscope unit with a sensation as though operating the microscope unit in a weightless environment, and the operability for the surgeon can be improved.

CITATION LIST

Patent Literature

Patent Literature 1: JP H8-266555A
Patent Literature 2: JP 2005-6960A

DISCLOSURE OF INVENTION

Technical Problem

Herein, the microscope units in the microscope devices described in Patent Literature 1 and 2 are optical, and the surgeon observes the operating site by directly peering into an eyepiece provided on the microscope unit. Hereinafter, a microscope device provided with an optical microscope unit will also be called an optical microscope device for the sake of convenience.

Meanwhile, in recent years, there are being developed microscope devices provided with an electronic imaging microscope unit equipped with an image sensor and capable of imaging the operating site electronically. With a microscope device provided with an electronic imaging microscope unit (hereinafter also called an electronic imaging microscope device for the sake of convenience), a picture of the operating site imaged by the microscope unit is displayed on a display device installed in the operating room, and the surgeon performs surgery while observing the picture of the operating site depicted on the display device.

With such an electronic imaging microscope device, to increase patient safety further, it is desirable to prepare a substitute means of observation to enable the continuation of surgery even in cases in which the picture of the operating site is no longer displayed normally on the display device for some reason. As the substitute means of observation, it is conceivable to prepare a separate optical microscope device in addition to the electronic imaging microscope device, for example.

However, making available a substitute microscope device leads to so increased costs. Also, since it is necessary to make preparations for the substitute microscope device in addition to the electronic imaging microscope device to use in the first place, the amount of work increases, and the burden on the medical staff becomes greater. Furthermore, since it is necessary to secure space to the install the substitute microscope device, the inside of the operating room becomes crowded.

Accordingly, the present disclosure proposes a new and improved surgical microscope device and surgical microscope system enabling observation of the operating site to be continued more easily in the case in which the picture of the operating site is no longer displayed normally.

Solution to Problem

According to the present disclosure, there is provided a surgical microscope device including: a microscope unit that images an observation target, and outputs a picture signal; a support unit that supports the microscope unit, and is configured as a balance arm; and an auxiliary observation device that is attachable to the microscope unit or the support unit, and is configured to enable observation of an observation range provided by the microscope unit.

In addition, according to the present disclosure, there is provided a surgical microscope system including: a microscope device, including a microscope unit that images an observation target and outputs a picture signal, a support unit that supports the microscope unit and is configured as a balance arm, and an auxiliary observation device that is attachable to the microscope unit or the support unit, and is configured to enable observation of an observation range provided by the microscope unit; and a display device that displays a picture based on the picture signal.

According to the present disclosure, in a surgical microscope device, there is provided an auxiliary observation device that is attachable to the microscope unit or the support unit, and is configured to enable observation of the observation range so provided by the microscope unit. Consequently, in the case in which the picture of the operating site is no longer displayed normally, the auxiliary observation device can be used to enable the continuation of surgery while observing the observation target (operating site) directly.

Advantageous Effects of Invention

According to the present disclosure as described above, in the case in which the picture of the operating site is no longer displayed normally, it becomes possible to continue observation of the operating site more easily. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
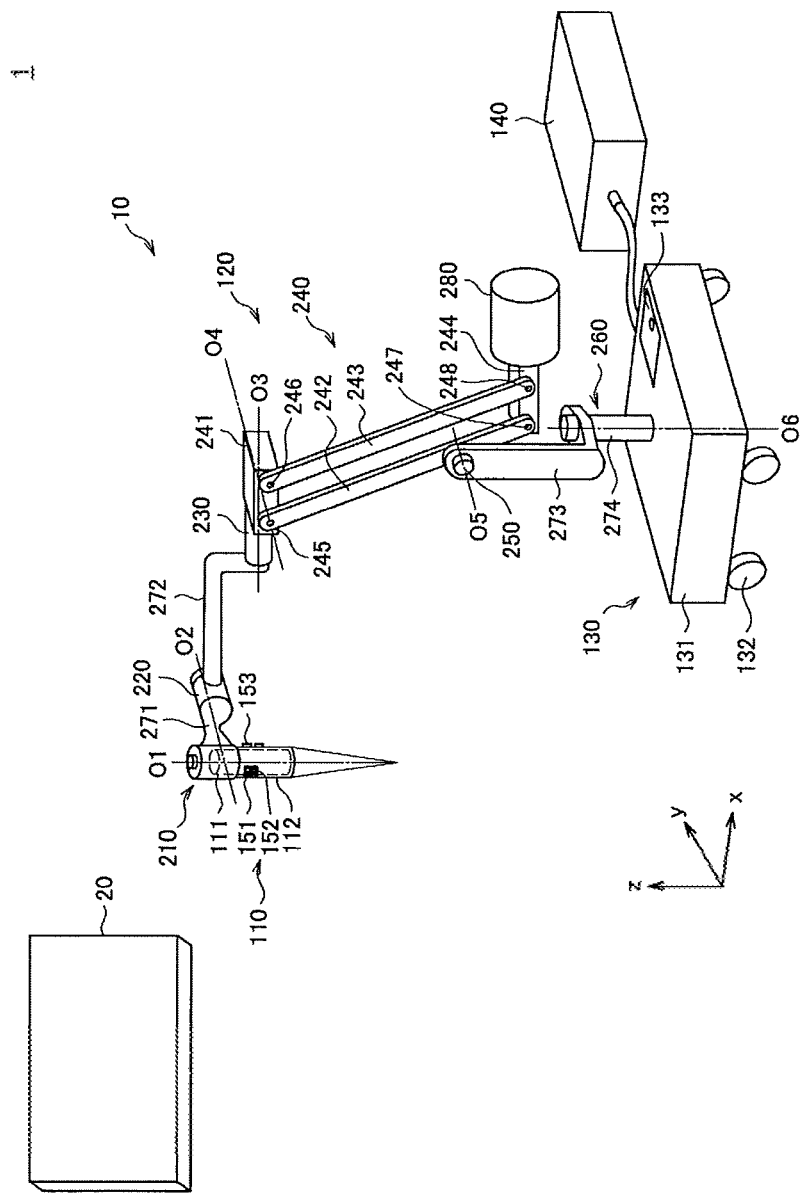
FIG. 1 is a diagram illustrating an exemplary configuration of a microscope system according to a first embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. First Embodiment
1-1. Overall configuration of microscope device
1-2. Configuration of auxiliary observation device
2. Second Embodiment
2-1. Configuration of auxiliary observation device
3. Third Embodiment
3-1. Configuration of auxiliary observation device
4. Fourth Embodiment
4-1. Configuration of auxiliary observation device
5. Supplemental remarks Note that in the following, the user who performs various operations on a microscope device according to the respective embodiments of the present disclosure is designated the surgeon for the sake of convenience. However, this designation does not limit the user who uses the microscope device, and the various operations on the microscope device may also be executed by any user, such as another member of the medical staff.

1. First Embodiment (1-1. Overall Configuration of Microscope Device)

With reference to FIG. 1, a configuration of a microscope system according to a first embodiment of the present disclosure will be described, and in addition, an overall configuration of a microscope device constituting such a microscope system will be described. FIG. 1 is a diagram illustrating an exemplary configuration of a microscope system according to a first embodiment.

Referring to FIG. 1, a microscope system 1 according to the first embodiment is made up of a microscope device 10 which supports a microscope unit 110 and which images an operating site of a patient with the microscope unit 110, and a display device 20 that displays a picture of the operating site imaged by the microscope device 10. During a surgery, the surgeon observes the operating site and performs various treatments on the operating site while referring to the picture imaged by the microscope device 10 and displayed on the display device 20.

(Display Device)

As described above, the display device 20 displays a picture of an operating site of a patient imaged by the microscope device 10. The display device 20 is installed in a location visible to the surgeon, such as on a wall of the operating room, for example. The type of the display device 20 is not particularly limited, and any of various known types of display devices may be used as the display device 20, such as a cathode ray tube (CRT) display device, a liquid crystal display device, a plasma display device, or an electroluminescence (EL) display device. Additionally, the display device 20 is not necessarily required to be installed inside the operating room, and may also be installed in a device used by being worn on the surgeon's body, such as a head-mounted display (HMD) or an eyeglasses-type wearable device.

(Microscope Device)

The microscope device 10 is provided with a microscope unit 110 for performing enlarged observation of an operating site of a patient, a support unit 120 (arm unit 120) that holds the microscope unit 110, a base unit 130 to which one end of the support unit 120 is connected and which supports the microscope unit 110 and the support unit 120, and a control device 140 that controls the operation of the microscope device 10. The microscope device 10 is a surgical microscope device for performing enlarged observation of an operating site of a patient during surgery.

(Base Unit 130)

The base unit 130 supports the microscope unit 110 and the support unit 120. The base unit 130 includes a platform 131 having a planar shape, and multiple casters 132 provided on the bottom face of the platform 131. One end of the support unit 120 is connected to the top face of the platform 131, while the microscope unit 110 is connected to the other end of the support unit 120 extending from the platform 131 (the front end). Also, the microscope device 10 is in contact with the floor through the casters 132, and is configured to be movable across the floor by the casters 132.

In addition, the platform 131 may be provided with a storage unit 133 for storing an auxiliary observation device 310 described later. In the case in which the picture of the operating site is no longer displayed normally, the surgeon is able to retrieve the auxiliary observation device 310 from the storage unit 133, appropriately attach the auxiliary observation device 310 to the microscope unit 110 or the support unit 120, use the auxiliary observation device 310 to observe the operating site, and continue surgery. Note that the auxiliary observation device 310 is described in further detail in (1-2. Configuration of auxiliary observation device) below.

Note that in the following description, the vertical direction with respect to the floor on which the microscope device 10 is installed is defined to be the z-axis direction. The z-axis direction is also called the up-and-down direction or the vertical direction. Additionally, the two mutually orthogonal directions to the z-axis direction are defined to be the x-axis direction and the y-axis direction. The direction parallel to the x-y plane is also called the horizontal direction.

(Microscope Unit 110)

The microscope unit 110 is made up of a microscope body for performing enlarged observation of an operating site of a patient. In the illustrated example, the optical axis direction of the microscope unit 110 is approximately aligned with the z-axis direction. The microscope unit 110 has a configuration corresponding to an electronic imaging microscope, and is made up of a barrel unit 112 having an approximately hollow round cylindrical shape, and an imaging unit 111 provided inside the barrel unit 112. Additionally, the imaging unit 111 is made up of an optical system such as an objective lens and a zoom lens, and an image sensor that captures an image of a subject (namely, the operating site) with light passing through the optical system.

The aperture on the bottom end of the barrel unit 112 is provided with a cover glass for protecting the imaging unit 111. A light source is also provided inside the barrel unit 112, and during imaging, the subject is irradiated with illuminating light radiating from the light source through the cover glass. Of this illuminating light, the light reflecting back from the subject is incident on the imaging unit 111 via the cover glass, and as a result, a signal corresponding to an image of the operating site (picture signal) is acquired by the imaging unit 111.

For the microscope unit 110, it is sufficient to apply a configuration corresponding to any of various known types of electronic imaging microscope units, and for this reason a detailed description thereof will be reduced or omitted herein. For example, any of various known types of image sensors may be applied as the image sensor of the imaging unit 111, such as a charge-coupled device (CCD) sensor or a complementary metal-oxide-semiconductor (CMOS) sensor. Additionally, the imaging unit 111 may also be configured as a stereo camera equipped with a pair of image sensors. Also, any of various known types of configurations may be applied to the optical system of the imaging unit 111. Furthermore, any of various types of functions typically provided in electronic imaging microscope units, such as an autofocus (AF) function and an optical zoom function, may be provided in the imaging unit 111.

The picture signal acquired by the microscope unit 110 is transmitted to the control device 140. In the control device 140, various types of image processing are performed, such as gamma correction and white balance adjustment, for example. In addition, in the control device 140, image processing such as enlargement and pixel interpolation related to an electronic zoom function may also be performed. The picture signal that has been subjected to image processing is transmitted to the display device 20 provided in the operating room, and a picture of the surgical site is displayed on the display device 20, appropriately magnified at a desired magnification by an optical zoom function and/or an electronic zoom function, for example. Note that the communication between the control device 140 and the display device 20 may be realized by any of various known wired or wireless methods.

Note that a processing circuit for performing the above image processing may be provided in the microscope unit 110, and the above image processing may be performed by the processing circuit of the microscope unit 110, without being performed by the control device 140. In this case, image information after suitable image processing has been performed in the processing circuit provided in the microscope unit 110 may be transmitted from the microscope unit 110 to the display device 20 provided in the operating room. Also, in this case, the communication between the microscope unit 110 and the display device 20 may be realized by any of various known wired or wireless methods.

Figure 3:
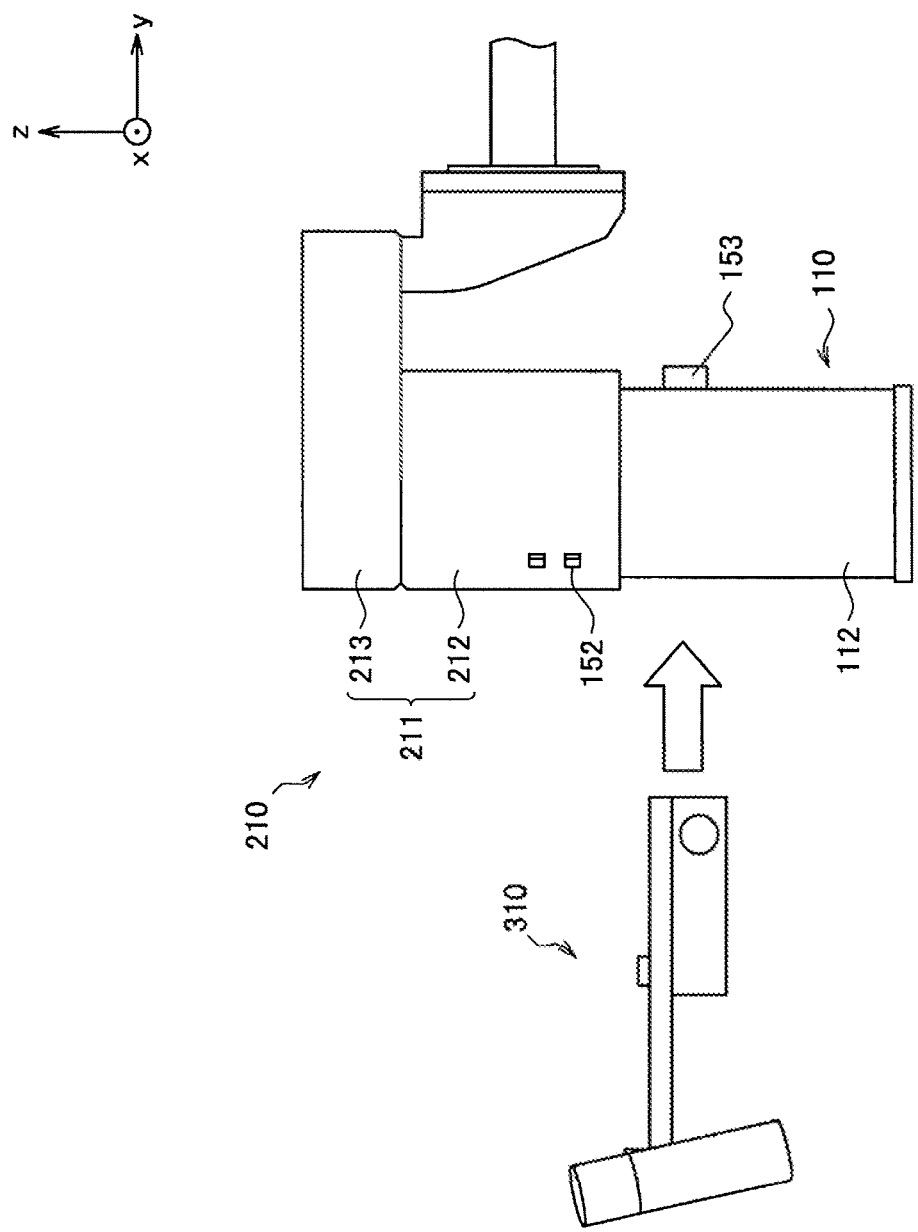
FIG. 3 is a diagram illustrating a method of attaching an auxiliary observation device according to a first embodiment to a microscope unit.

The microscope unit 110 is provided with various types of switches for controlling the operation of the microscope unit 110. For example, the microscope unit 110 is provided with a zoom switch 151 (zoom SW 151) and a focus switch 152 (focus SW 152) for adjusting the imaging parameters of the microscope unit 110, as well as an operating mode toggle switch 153 (operation mode toggle SW 153) for toggling the operating mode of the support unit 120. Note that FIG. 1 illustrates the zoom SW 151 and the focus SW 152 arranged on the outer side face of the barrel unit 112 for the sake of convenience, but in the first embodiment, these switches may also be provided on the outer side face of an approximately hollow round cylindrical housing constituting a first rotation axis unit 210, as illustrated in FIG. 3 and the like described later.

The surgeon, by operating the zoom SW 151 and the focus SW 152, is able to adjust the magnification and the focal length of the microscope unit 110, respectively. Also, by operating the operating mode toggle SW 153, the surgeon is able to toggle the operating mode of the support unit 120 between a locked mode and a free mode.

Herein, the locked mode is an operating mode in which the position and the attitude of the microscope unit 110 are locked by using a brake to restrain rotation about each rotation axis provided in the support unit 120. The free mode is an operating mode in which the brake is released, thereby allowing free rotation about each rotation axis provided in the support unit 120, and enabling the surgeon to adjust the position and the attitude of the microscope unit 110 with direct operations. Herein, direct operations mean operations in which the surgeon grips the microscope unit 110 with his or her hand, for example, and directly moves the microscope unit 110. For example, the operating mode of the support unit 120 becomes the free mode while the surgeon is pressing the operating mode toggle SW 153, and the operating mode of the support unit 120 becomes the locked mode while the surgeon releases his or her hand from the operating mode toggle SW 153.

Note that these switches are not necessarily required to be provided on the microscope unit 110. In the first embodiment, it is sufficient for the microscope device 10 to be provided with a mechanism for accepting operating input having functions similar to these switches, and the specific configuration of such a mechanism is not limited. For example, these switches may also be provided on another section of the microscope device 10. As another example, an input device such as a remote control may be used, and commands corresponding to these switches may be input into the microscope device 10 remotely.

Also, although the barrel unit 112 of the microscope unit 110 is illustrated as a simple hollow round cylindrical member in FIG. 1 for the sake of simplicity, in actuality, the barrel unit 112 may also be shaped innovatively to be gripped more easily by the surgeon. For example, when in the free mode, operations of moving the microscope unit 110 with the surgeon gripping the barrel unit 112 directly in hand may be anticipated. At this point, since the surgeon performs an operation of moving the microscope unit 110 while pressing the operating mode toggle SW 153, the shape of the barrel unit 112 and the placement of the operating mode toggle SW 153 may be decided appropriately with consideration for operability by the surgeon while in the free mode. In addition, the placement of the zoom SW 151 and the focus SW 152 may be decided appropriately with similar consideration for operability by the surgeon.

(Control Device 140)

The control device 140 is made up of a processor, such as a central processing unit (CPU) or a digital signal processor (DSP), for example, or a control board on which these processors are mounted together with components such as memory. By executing computational processing according to a certain program, the control device 140 controls the operation of the microscope device 10.

For example, the control device 140 includes a function of toggling the operating mode of the support unit 120 described above by controlling the driving of the brake provided in each joint unit of the support unit 120 in response to operating input performed by the surgeon via the above operating mode toggle SW 153. As another example, the control device 140 includes a function of appropriately driving the optical system in the imaging unit 111 of the microscope unit 110 to adjust the magnification and the focal length of the microscope unit 110 in response to so operating input performed by the surgeon via the above zoom SW 151 and focus SW 152. In addition, the control device 140 includes a function of performing various types of image processing on a picture signal imaged by the microscope unit 110, and transmitting the processed picture signal to the display device 20 provided in the operating room.

Note that in the illustrated example, the control device 140 is provided as a different configuration from the microscope unit 110, the support unit 120, and the base unit 130, and is connected to the base unit 130 by a cable. However, the first embodiment is not limited to such an example. For example, a processor, a control board, or the like that realizes functions similar to the control device 140 may also be disposed inside the base unit 130. Additionally, by incorporating a processor, a control board, or the like that realizes functions similar to the control device 140 into the microscope unit 110 internally, the control device 140 and the microscope unit may be configured in an integrated manner.

(Support Unit 120)

The support unit 120 holds the microscope unit 110, and moves the microscope unit 110 three-dimensionally while also locking the position and the attitude of the microscope unit 110 after moving. In the first embodiment, the support unit 120 is configured as a balance arm having six degrees of freedom. However, the first embodiment is not limited to such an example, and the support unit 120 may also be configured to have a different number of degrees of freedom. By configuring the support unit 120 as a balance arm and taking a configuration having an equilibrium of moments for the microscope unit 110 and the support unit 120 as a whole, it becomes possible to move the microscope unit 110 with less external force, and operability for the surgeon can be improved further.

The support unit 120 is provided with six rotation axes corresponding to the six degrees of freedom (first axis $O_1$, second axis $O_2$, third axis $O_2$, fourth axis $O_4$, fifth axis $O_5$, and sixth axis $O_6$). In the following description, for the sake of convenience, the members constituting each rotation axis will be referred to collectively as the rotation axis unit. For example, the rotation axis unit may be made up of components such as a bearing, a shaft rotatably inserted into the bearing, and a brake that restrains rotation about the rotation axis. The parallelogram link mechanism 240 described later may also be considered to be one of the rotation axis units.

The support unit 120 is made up of a first rotation axis unit 210, a second rotation axis unit 220, a third rotation axis unit 230, a fourth rotation axis unit 240, a fifth rotation axis unit 250, and a sixth rotation axis unit 260 corresponding to each rotation axis, a first arm unit 271, a second arm unit 272, a third arm unit 273, and a fourth arm unit 274 rotatably connected to each other by the first rotation axis unit 210 to the sixth rotation axis unit 260, and a counterweight 280 for maintaining the equilibrium of moments for the microscope unit 110 and the support unit 120 as a whole. Note that the fourth rotation axis unit 240 corresponds to the parallelogram link mechanism 240.

Note that in the following description, when describing the configuration of the support unit 120, the side on which the microscope unit 110 is provided may also be called the front end side or the front end unit, while the side near the base unit 130 may also be called the base end side or the base end unit.

The first rotation axis unit 210 has an approximately hollow round cylindrical shape, and is connected to the base end unit of the barrel unit 112 of the microscope unit 110 so that the central axis is approximately aligned with the central axis of the barrel unit 112 of the microscope unit 110. The first rotation axis unit 210 rotatably supports the microscope unit 110, with the rotation axis direction (first axis $O_1$ direction) being a direction approximately aligned with the optical axis of the microscope unit 110. In the example illustrated in FIG. 1, the first axis $O_1$ is provided as a rotation axis approximately parallel to the z-axis. By having the microscope unit 110 rotate about the first axis O by the first rotation axis unit 210, so the direction of images captured by the microscope unit 110 is adjusted.

Note that in the illustrated example, part of the imaging unit 11 of the microscope unit 110 is stored inside the hollow round cylindrical housing constituting the first rotation axis unit 210. In other words, the microscope unit 110 and the first rotation axis unit 210 are configured as an integrated member. However, the first embodiment is not limited to such an example, and the first rotation axis unit 210 and the microscope unit 110 may also be configured as mutually individual members.

The front end of the first arm unit 271 extending in a direction approximately perpendicular to the first axis O is connected to the first rotation axis unit 210. Also, at the base end of the first arm unit 271, there is provided the second rotation axis unit 220 that rotatably supports the first arm unit 271, with the rotation axis direction (second axis $O_2$ direction) being a direction approximately parallel to the extension direction of the first arm unit 271. The second axis $O_2$ is a rotation axis approximately perpendicular to the first axis $O_1$, and in the example illustrated in FIG. 1, is provided as a rotation axis approximately parallel to the y-axis. By having the microscope unit 110 and the first arm unit 271 rotate about the second axis $O_2$ as a rotation axis by the second rotation axis unit 220, the position in the x-axis direction of the microscope unit 110 is adjusted.

The front end of the second arm unit 272 extending in a direction approximately perpendicular to both the first axis $O_1$ and the second axis $O_2$ is connected to the second rotation axis unit 220. Also, the base end side of the second arm unit 272 is bent in an L-shape, and at the position corresponding to the bent short side, there is provided the third rotation axis unit 230 that rotatably supports the second arm unit 272, with the rotation axis direction (third axis $O_3$ direction) being a direction approximately parallel to the extension direction of the part corresponding to the long side of the second arm unit 272. The third axis $O_3$ is a rotation axis approximately perpendicular to the first axis $O_1$ and the second axis $O_2$, and in the example illustrated in FIG. 1, is provided as a rotation axis approximately parallel to the x-axis. By having the microscope unit 110, the first arm unit 271, and the second arm unit 272 rotate about the third axis $O_3$ as a rotation axis by the third rotation axis unit 230, the position in the y-axis direction of the microscope unit 110 is adjusted.

In this way, the support unit 120 is configured so that as a result of rotation about the second axis $O_2$ and the third axis $O_3$ being controlled respectively, the attitude of the microscope unit 110 is controlled. In other words, the second rotation axis unit 220 and the third rotation axis unit 230 may be the rotation axis units that prescribe the attitude of the microscope unit 110.

The front end of the top side of the parallelogram link mechanism 240 is connected to the base end side of the third rotation axis unit 230. The parallelogram link mechanism 240 is made up of four arms (arms 241, 242, 243, and 244) arranged in a parallelogram shape, and four joint units (joint units 245, 246, 247, and 248) respectively provided at positions corresponding to the approximate vertices of the parallelogram.

The front end of the arm 241 extending in a direction approximately parallel to the third axis $O_3$ is connected to the third rotation axis unit 230. The joint unit 245 is provided near the front end of the arm 241, while the joint unit 246 is provided near the base end of the arm 241. The front ends of the arms 242 and 243 are connected to the joint units 245 and 246, respectively, allowing rotation about respective rotation axes (fourth axis $O_4$) approximately perpendicular to the extension direction of the arm 241 and approximately parallel to each other. Furthermore, the joint units 247 and 248 are provided on the base ends of the arms 242 and 243, respectively. The front end and the base end of the arm 244 are connected to these joint units 247 and 248, respectively, allowing rotation about the fourth axis $O_4$, and also approximately parallel to the arm 241.

In this way, the four joint units constituting the parallelogram link mechanism 240 include rotation axes (fourth axis $O_4$) approximately parallel to each other and approximately in the same direction, which operate in conjunction with each other about the fourth axis $O_4$. In the example illustrated in FIG. 1, the fourth axis $O_4$ is provided as a rotation axis approximately parallel to the y-axis. In other words, the parallelogram link mechanism 240 includes multiple joint units that rotate in conjunction with each other around rotation axes disposed in mutually different positions but in the same direction, and fulfills the role of a transmission mechanism that transmits an operation on one end to the other end. By providing the parallelogram link mechanism 240, the motion of the configuration on the front end side past the parallelogram link mechanism 240 (that is, the microscope unit 110, the first rotation axis unit 210, the second rotation axis unit 220, the third rotation axis unit 230, the first arm unit 271, and the second arm unit 272) is transmitted to the base end side of the parallelogram link mechanism 240.

On a part of the arm 242 separated a certain distance from the base end, there is provided the fifth rotation axis unit 250 that rotatably supports the parallelogram link mechanism 240, with the rotation axis direction (fifth axis $O_5$ direction) being a direction perpendicular to the extension direction of the arm 242. The fifth axis $O_5$ is a rotation axis approximately parallel to the fourth axis $O_4$, and in the example illustrated in FIG. 1, is provided as a rotation axis approximately parallel to the y-axis. The front end of the third arm unit 273 running in the z-axis direction is connected to the fifth rotation axis unit 250, and the microscope unit 110, the first arm unit 271, the second arm unit 272, and the parallelogram link mechanism 240 are allowed to rotate with respect to the third arm unit 273 via the fifth rotation axis unit 250, about the fifth axis $O_5$ as the rotation axis.

The third arm unit 273 is approximately L-shaped, with the base end side bent to be approximately parallel to the floor. The sixth rotation axis unit 260 that allows the third arm unit 273 to rotate about a rotation axis (sixth axis $O_6$) orthogonal to the fifth axis $O_5$ is connected to the face approximately parallel to the floor on the third arm unit 273. In the example illustrated in FIG. 1, the sixth axis $O_6$ is provided as a rotation axis approximately parallel to the z-axis.

In the illustrated example, the sixth rotation axis unit 260 is integrated with the fourth arm unit 274 that extends in the vertical direction. In other words, the front end of the fourth arm unit 274 is connected to the face approximately parallel to the floor on the base end of the third arm unit 273. Also, the base end of the fourth arm unit 274 is connected to the top face of the platform 131 of the base unit 130. With this configuration, the microscope unit 110, the first arm unit 271, the second arm unit 272, the parallelogram link mechanism 240, and the third arm unit 273 rotate with respect to the base unit 130 via the sixth rotation axis unit 260, about the sixth axis $O_6$ as the rotation axis.

The arm 244 constituting the bottom side of the parallelogram link mechanism 240 is formed to be longer than the arm 241 constituting the top side, and the end of the arm 242 which is positioned diagonally opposite the part where the third rotation axis unit 230 is connected on the parallelogram link mechanism 240 is extended to the outside of the parallelogram link mechanism 240. On the extended end of the arm 244, the counterweight 280 is provided. The mass and the placement of the counterweight 280 are adjusted so that the rotation moment produced about the fourth axis $O_4$ and the rotation moment produced about the fifth axis $O_5$ may be canceled out by the mass of the configuration disposed past the front end side of the counterweight 280 itself (that is, the microscope unit 110, the first rotation axis unit 210, the second rotation axis unit 220, the third rotation axis unit 230, the first arm unit 271, the second arm unit 272, and the parallelogram link mechanism 240).

In addition, the placement of the fifth rotation axis unit 250 is adjusted so that the center of gravity of the configuration disposed farther on the front end side than the fifth rotation axis unit 250 is positioned on the fifth axis $O_5$. Furthermore, the placement of the sixth rotation axis unit 260 is adjusted so that the center of so gravity of the configuration disposed farther on the front end side than the sixth rotation axis unit 260 is positioned on the sixth axis $O_6$.

By configuring the mass and placement of the counterweight 280, the placement of the fifth rotation axis unit 250, and the placement of the sixth rotation axis unit 260 in this way, the support unit 120 may be configured as a balance arm that maintains the equilibrium of moments for the microscope unit 110 and the support unit 120 as a whole. By configuring the support unit 120 as a balance arm, in the case in which the surgeon attempts to move the microscope unit 110 with a direct operation, the surgeon becomes able to move the microscope unit 110 with less external force, almost like a weightless state. Consequently, user operability can be improved.

Each of the first rotation axis unit 210 to the sixth rotation axis unit 260 of the support unit 120 is provided with a brake that restrains rotation in the first rotation axis unit 210 to the sixth rotation axis unit 260, respectively. Note that for the parallelogram link mechanism 240, since the four joint units (joint units 245 to 248) rotate in conjunction with each other, it is sufficient to provide the brake for the parallelogram link mechanism 240 on at least one of these four joint units. The driving of these brakes is controlled by the control device 140. By releasing these brakes all at once under control from the control device 140, the operating mode of the support unit 120 switches to the free mode. Also, by similarly driving these brakes all at once under control from the control device 140, the operating mode of the support unit 120 switches to the locked mode.

Note that for the brakes provided in the first rotation axis unit 210 to the sixth rotation axis unit 260, any of various types of brakes used in a typical balance arm may be applied, and the specific mechanism is not limited. For example, these brakes may be mechanically driven, or may also be electrically driven electromagnetic brakes.

(1-2. Configuration of Auxiliary Observation Device)

As described above, in the microscope system 1, a picture of the operating site imaged by the microscope unit 110 is displayed on the display device 20. However, during an emergency such as a power failure, for example, or in a case in which a malfunction occurs in one of the devices constituting the microscope system 1, a situation is anticipated in which the picture of the operating site is no longer displayed normally on the display device 20.

In the microscope system 1, to further increase patient safety, it is desirable to be able to continue surgery, even in cases in which the picture of the operating site is no longer displayed normally for some reason. Note that conceivable reasons why the picture of the operating site is no longer display normally include a malfunction in the image sensor of the microscope unit 110, a malfunction in the display device 20, and/or a malfunction in the communication between the microscope device 10 and the display device 20.

Accordingly, in the present disclosure, as a substitute means of observations in the case in which the picture of the operating site is no longer display normally, there is provided an auxiliary observation device that is attachable to the microscope unit 110 or the support unit 120. The auxiliary observation device is a loupe, for example, and in the case in which the picture of the operating site is no longer displayed normally, the auxiliary observation device can be attached to the microscope unit 110 or the support unit 120, thereby enabling the surgeon to continue surgery while peering directly into the auxiliary observation device.

Note that in the following, the case in which the auxiliary observation device according to each embodiment of the present disclosure is a loupe will be described as an example. However, in the present disclosure, the auxiliary observation device is not limited to a loupe. It is sufficient for the auxiliary observation device to be provided with an optical system enabling enlarged observation of the operating site by having the surgeon peer directly into the device, so and the specific configuration may be arbitrary.

Figure 2:
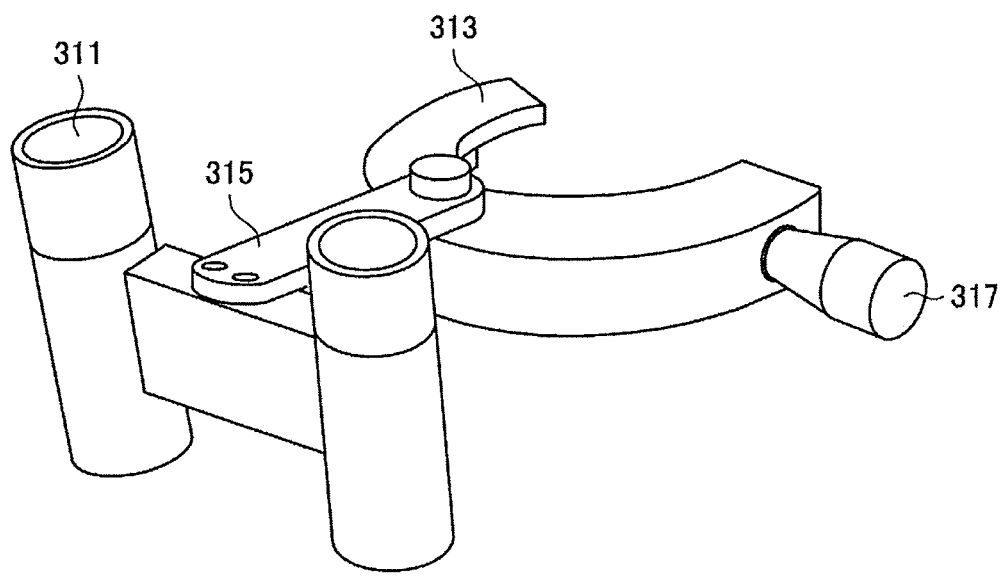
FIG. 2 is a perspective diagram illustrating a configuration of an auxiliary observation device according to a first embodiment.
Figure 4:
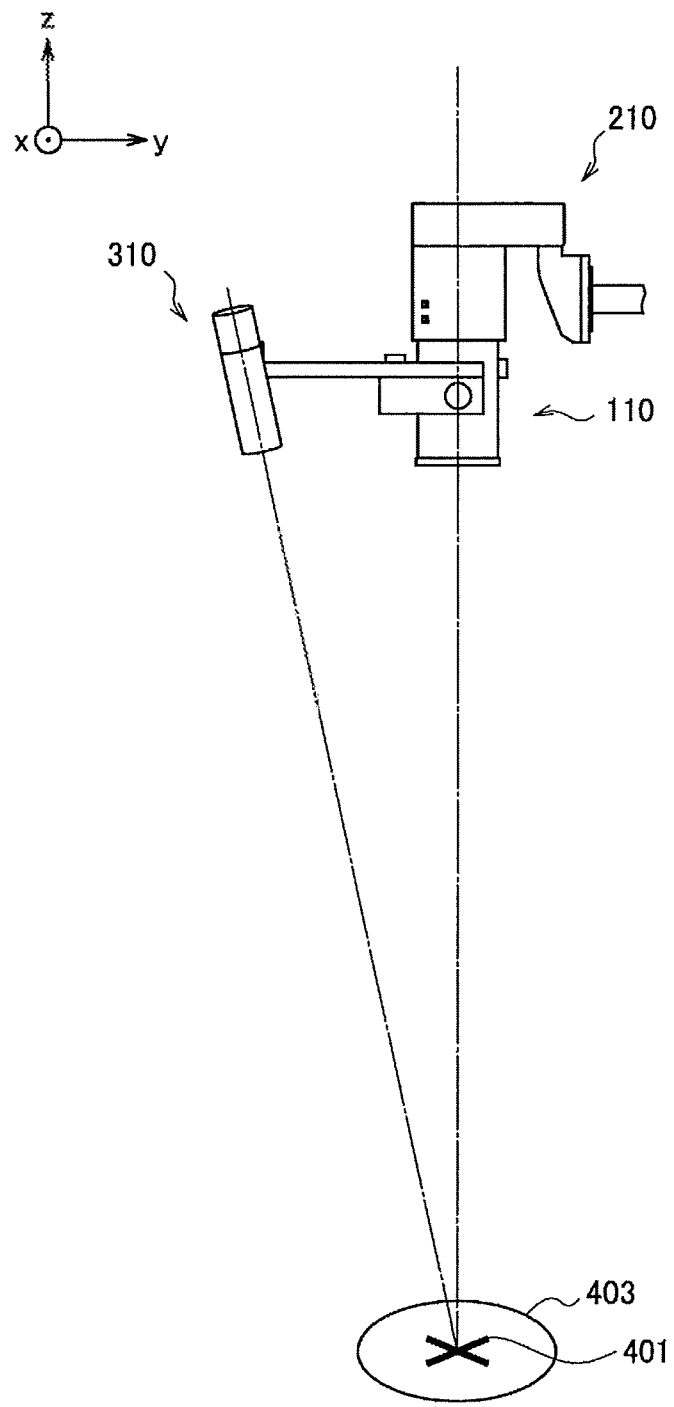
FIG. 4 is a profile diagram illustrating how an auxiliary observation device according to a first embodiment is attached to a microscope unit.

A configuration of an auxiliary observation device according to the first embodiment will be described with reference to FIGS. 2 to 4. FIG. 2 is a perspective diagram illustrating a configuration of an auxiliary observation device according to the first embodiment. FIG. 3 is a diagram illustrating a method of attaching an auxiliary observation device according to the first embodiment to the microscope unit 110. FIG. 4 is a profile diagram illustrating how an auxiliary observation device according to the first embodiment is attached to the microscope unit 110. Note that FIGS. 3 and 4 illustrate an extraction of only the microscope unit 110 and the first rotation axis unit 210 from the microscope device 10 illustrated in FIG. 1. However, in FIGS. 3 and 4, the configuration of the microscope unit 110 and the first rotation axis unit 210 is illustrated in greater detail than FIG. 1.

Referring to FIG. 2, the auxiliary observation device 310 according to the first embodiment is made up of a lens barrel unit 311, an attachment mechanism unit 313, a connecting unit 315 that connects the lens barrel unit 311 and the attachment mechanism unit 313, and a securing member 317 for securing the auxiliary observation device 310 to the microscope unit 110.

The lens barrel unit 311 is made up of a pair of lens barrels, inside of which is provided an optical system such as lenses for performing enlarged observation of the operating site. The surgeon, by peering into the lens barrel unit 311 from an eyepiece provided on the top end, is able to observe the state of the operating site appropriately magnified by the optical system provided inside the lens barrel unit 311. Note that, for the sake of simplicity, the specific configuration is omitted from illustration, but the lens barrel unit 311 preferably is provided with an interpupillary adjustment mechanism enabling the distance between the lens barrels to be adjusted in accordance with the interpupillary distance of the surgeon. When using the auxiliary observation device 310, by appropriately adjusting the distance between the lens barrels with the interpupillary adjustment mechanism, the surgeon is able to so observe the operating site more clearly.

The connecting unit 315 is a rod-shaped member, one end of which is connected to the lens barrel unit 311, while the other end is connected to the attachment mechanism unit 313.

The attachment mechanism unit 313 is a mechanism for attaching the auxiliary observation device 310 to the microscope unit 110. The attachment mechanism unit 313 has a circular arc shape corresponding to the outer circumference of the hollow round cylindrical barrel unit 112 of the microscope unit 110. When attaching the auxiliary observation device 310 to the microscope unit 110, as illustrated in FIGS. 3 and 4, the auxiliary observation device 310 is mounted onto the microscope unit 110 so that a partial region along the outer circumference of the barrel unit 112 of the microscope unit 110 is covered by the circular arc shape of the attachment mechanism unit 313.

The securing member 317 is a bolt, for example, and is a member for securing the auxiliary observation device 310 to the microscope unit 110. Specifically, an opening is provided in a partial region of the face of the attachment mechanism unit 313 that opposes the side wall of the barrel unit 112 of the microscope unit 110, and a screw thread is cut into the inner wall of the opening. As illustrated in FIGS. 3 and 4, in the state in which the auxiliary observation device 310 is mounted onto the barrel unit 112 of the microscope unit 110, by inserting and screwing the securing member 317 into the opening of the attachment mechanism unit 313 until the tip abuts the side wall of the barrel unit 112, the auxiliary observation device 310 is secured to the microscope unit 110.

When the auxiliary observation device 310 is attached to the microscope unit 110, the connection angle of the lens barrel unit 311 of the auxiliary observation device 310 with respect to the connecting unit 315 (that is, the tilt angle with respect to the optical axis of the microscope unit 110), the optical system inside the lens barrel unit 311, and the like are adjusted to allow at least part of the observation range provided by the microscope unit 110 to be observed with the lens barrel unit 311.

Specifically, as illustrated in FIG. 4, when the auxiliary observation device 310 is attached to the microscope unit 110, the arrangement angle with respect to the connecting unit 315 and the like may be adjusted so that the optical axis of the lens barrel unit 311 of the auxiliary observation device 310 intersects with the optical axis of the microscope unit 110 at a position that roughly corresponds to an observation target 401 (that is, the operating site). Additionally, the magnification, focal length, and the like of the optical system provided inside the lens barrel unit 311 may be adjusted in consideration of the observation range provided by the microscope unit 110.

Herein, in the first embodiment, the optical system of the lens barrel unit 311 may also not be provided with a magnification adjustment function and a focal length adjustment function, and the magnification and the focal length may be fixed. By configuring the lens barrel unit 311 in this way, the configuration of the auxiliary observation device 310 can be simplified. However, the imaging unit 111 of the microscope unit 110 may be provided with a magnification adjustment function and a focal length adjustment function. Consequently, in the case in which the magnification and the focal length of the lens barrel unit 311 are fixed, it is difficult to configure the optical system of the lens barrel unit 311 so that the entire observation range of the microscope unit 110 is observable with the lens barrel unit 311. Thus, when actually designing the optical system of the lens barrel unit 311, the optical system may be designed to have an appropriate magnification and focal length enabling the continuation of surgery, for example. In this case, it is not strictly necessary for the entire observation range of the microscope unit 110 to be observable with the lens barrel unit 311, and it is sufficient for at least part of the observation range to be observable.

In this way, by configuring the auxiliary observation device 310 to enable the observation of at least part of the observation range provided by the microscope unit 110, when the surgeon attaches the auxiliary observation device 310 and peers into the lens barrel unit 311 in a case in which the picture of the operating site is no longer displayed normally, the surgeon is able to observe a range corresponding to the range that had been imaged by the microscope unit 110 up until that time, and is able to continue surgery smoothly.

Note that in the first embodiment, in the case in which the light source of the microscope unit 110 is still functioning normally even through the picture of the operating site is no longer displayed normally, observation of the observation target 401 may be conducted with the auxiliary observation device 310 in a state in which the observation target 401 is irradiated with illuminating light from the microscope unit 110 using the light source. FIG. 4 illustrates a simulation of an irradiated range 403 irradiated by illuminating light.

Herein, the configuration of the microscope unit 110 and the first rotation axis unit 210 will be described in greater detail with reference to FIGS. 3 and 4. As described in (1-1. Overall configuration of microscope device) above, the microscope unit 110 is made up of a barrel unit 112 having an approximately hollow round cylindrical shape, and an imaging unit provided inside the barrel unit 112. The first rotation axis unit 210 is connected to the base end unit of the barrel unit 112 of the microscope unit 110. At this point, part of the imaging unit of the microscope unit 110 is stored inside the hollow round cylindrical housing 211 constituting the first rotation axis unit 210. In other words, the microscope unit 110 and the first rotation axis unit 210 are configured as an integrated member. Note that since the imaging unit is provided inside the microscope unit 110 and the housing of the first rotation axis unit 210 in this way, in FIGS. 3 and 4, illustration of the imaging unit is omitted to keep the drawings from becoming complicated.

The first rotation axis unit 210 rotatably supports the microscope unit 110 so about the first axis $O_1$, and in this case, the housing 211 constituting the first rotation axis unit 210 is configured so that a section of a certain length from the bottom end of (hereinafter designated the rotating unit 212) rotates together with the microscope unit 110, while a section above the rotating unit 212 is a section that rotatably supports the microscope unit 110 and the rotating unit 212 about the first axis $O_1$ (hereinafter designated the fixed unit 213). The first arm unit 271 illustrated in FIG. 1 (not illustrated in FIG. 2) is connected to the fixed unit 213 of the first rotation axis unit 210. Also, part of the imaging unit of the microscope unit 110 may be stored inside the rotating unit 212 of the first rotation axis unit 210.

As described above, the auxiliary observation device 310 according to the first embodiment is attached to the barrel unit 112, and thus is able to be rotated about the first axis $O_1$ together with the microscope unit 110. Consequently, after attaching the auxiliary observation device 310 to the microscope unit 110, by rotating the microscope unit 110 and the auxiliary observation device 310 about the first axis $O_1$, the observation range provided by the auxiliary observation device 310 can be adjusted easily, making it possible to continue surgery more smoothly.

The above thus describes a configuration of the auxiliary observation device 310 according to the first embodiment with reference to FIGS. 2 to 4. As described above, according to the first embodiment, there is provided an auxiliary observation device 310 attached to the microscope unit 110 in a case in which the picture of the operating site is no longer displayed normally. In the case in which the picture of the operating site is no longer displayed normally, the surgeon is able to continue surgery using the auxiliary observation device 310. After that, in a case in which the state of the picture of the operating site not being displayed normally is resolved (for example, in a case in which a replacement for a device that has malfunctioned is prepared, or a power failure or the like is resolved), it is sufficient to use the restored microscope system 1 to continue surgery. In this way, according to the first embodiment, in a case in which the picture of the operating site is no longer displayed normally, surgery can be continued as much as possible until the state is resolved, and patient safety during surgery can be improved further.

At this point, as the substitute means of observation in the case in which the picture of the operating site is no longer displayed normally, devices other than the auxiliary observation device 310, such as a head-mounted loupe worn on the surgeon's head, or another optical microscope device, for example, are conceivable. However, in the case of observing the operating site with a head-mounted loupe, to continue observing the operating site from a fixed position, it is necessary to keep constant the relative position of the surgeon's head with respect to operating site. Since the field of view of a loupe is limited, once the position of the head is moved, capturing the operating site in the field of observation again is not easy, and for a surgeon who is not particularly accustomed to using a head-mounted loupe, such a head-mounted loupe is not considered easy to use.

On the other hand, the case of using a substitute optical microscope device lead to increased cost equal to the cost of making available such a substitute microscope device. Also, since it is also necessary to prepare the substitute microscope device before surgery, the workload on the medical staff increases. Furthermore, since it is necessary to secure space to the install the substitute microscope device, the inside of the operating room becomes crowded.

In contrast, according to the first embodiment, as described above, the auxiliary observation device 310 is provided as a substitute means of observation in the case in which the picture of the operating site is no longer displayed normally. The auxiliary observation device 310 can be attached to the microscope unit 110 of the microscope device 10 with a simple operation, and the surgeon is able to continue observation of the operating site immediately using the auxiliary observation device 310.

At this point, in the case of using the auxiliary observation device 310, once the position of the microscope unit 110 has been set, the relative positional so relationship of the operating site and the auxiliary observation device 310 can be locked, and thus even if the surgeon briefly moves his or her head away from the auxiliary observation device 310, the surgeon is able to observe the operating site again immediately by peering into the auxiliary observation device 310. Consequently, there is no nuisance like that of the head-mounted loupe described above. Also, the auxiliary observation device 310 can be made available at low cost compared to a substitute microscope device, and furthermore does not require advance preparation or the like. Additionally, the auxiliary observation device 310 may be configured compactly and a smaller space is sufficient as a storage location, and thus a situation in which the inside of the operating room becomes crowded can also be avoided.

In this way, by using the auxiliary observation device 310 as a substitute means of observation, it becomes possible to continue the observation of the operating site more easily compared to the case of using a head-mounted loupe or another optical microscope device.

Note that in the related art, there is known an endoscopic device in which, instead of the microscope unit 110, an endoscope is supported by the support unit 120 as illustrated in FIG. 1. Likewise with such an endoscopic device, similarly to the microscope device 10, it is desirable to be able to continue surgery even in the case in which the picture of the operating site is no longer displayed normally. However, although dependent on the site targeted for surgery and the surgical technique, in an endoscopic device, in the case in which the picture of the operating site is no longer displayed normally, there is a possibility that surgery can be continued by proceeding to abdominal or cranial surgery, for example. In other words, with an endoscopic device, in the case in which the picture of the operating site is no longer displayed normally, there is a possibility that surgery can be continued without necessarily using the auxiliary observation device 310.

On the other hand, with the microscope device 10, since a substitute means so such as abdominal or cranial surgery for an endoscopic device does not exist, in the case in which the picture of the operating site is no longer displayed normally, surgery cannot be continued unless enlarged observation of the operating site is performed by some method. In this way, the auxiliary observation device 310 is considered to exhibit particularly advantageous effects by being used for a microscope device 10 in which abdominal or cranial surgery is presupposed.

Note that the auxiliary observation device 310 is kept inside a storage unit 133 provided in the microscope device 10, as illustrated in FIG. 1, for example. In this way, by keeping the auxiliary observation device 310 close to the surgeon, in the case in which the picture of the operating site is no longer displayed normally, the surgeon is able to retrieve and attach the auxiliary observation device 310 to the microscope unit 110 immediately. However, the storage location of the auxiliary observation device 310 is not limited to such an example, and the auxiliary observation device 310 may also be stored in an arbitrary location that is easily retrievable during an emergency, such as a certain location inside the operating room, for example.

Note that inside the storage unit 133, a manual describing information such as how to attach and how to use the auxiliary observation device 310 may also be kept together with the auxiliary observation device 310. Since the auxiliary observation device 310 is a device which may be used only during an emergency in the case in which the picture of the operating site is no longer displayed normally, ordinarily, it is anticipated that the surgeon will not have a firm grasp on how to use the auxiliary observation device 310. In this way, keeping a manual in a location allowing easy reference by the surgeon is considered to be extremely useful to the surgeon.

2. Second Embodiment

A second embodiment of the present disclosure will now be described. Note that the second embodiment corresponds to a modification of the attachment position of the auxiliary observation device with respect to the first embodiment described above, and other features (such as the configuration of the microscope system 1 and the overall configuration of the microscope device 10, for example) are similar to the first embodiment. Consequently, in the following description of the second embodiment, the features that differ from the first embodiment will be described primarily, whereas detailed description of features that overlap with the first embodiment will be reduced or omitted.

(2-1. Configuration of Auxiliary Observation Device)

Figure 5:
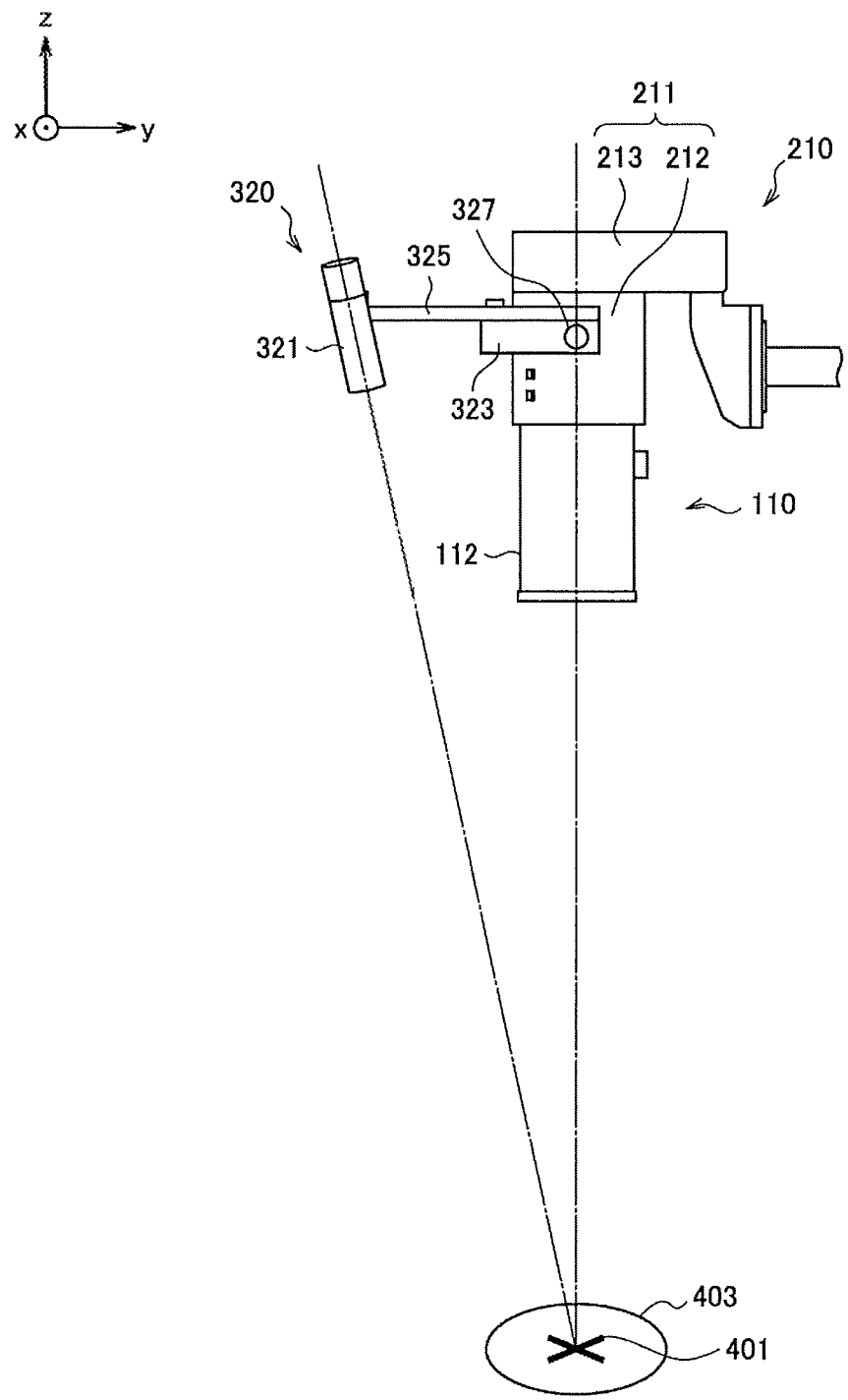
FIG. 5 is a profile diagram illustrating how an auxiliary observation device according to a second embodiment is attached to a first rotation axis unit.

A configuration of an auxiliary observation device according to the second embodiment will be described with reference to FIG. 5. FIG. 5 is a profile diagram illustrating how an auxiliary observation device according to the second embodiment is attached to the first rotation axis unit 210. Note that similarly to FIGS. 3 and 4, FIG. 5 illustrates an extraction of only the microscope unit 110 and the first rotation axis unit 210 from the microscope device 10 illustrated in FIG. 1. Since the configuration of the microscope unit 110 and the first rotation axis unit 210 is similar to that which is described in the above (1-2. Configuration of auxiliary observation device) with reference to FIGS. 3 and 4, detailed description will be reduced or omitted herein. Also, similarly to FIG. 3, FIG. 4 illustrates the observation target 401 as well as the irradiated range 403 irradiated by illuminating light from the microscope unit 110.

Referring to FIG. 5, an auxiliary observation device 320 according to the second embodiment is attached to the housing 211 constituting the first rotation axis unit 210. More specifically, in the second embodiment, the auxiliary observation device 320 is attached to the rotating unit 212 of the housing 211 constituting the first rotation axis unit 210.

Note that the configuration of the auxiliary observation device 320 is mostly similar to the configuration of the auxiliary observation device 310 according to the first embodiment. Specifically, the auxiliary observation device 320 is made up of a lens barrel unit 321, an attachment mechanism unit 323, a connecting unit 325 that connects the lens barrel unit 321 and the attachment mechanism unit 323, and a securing member 327 for securing the auxiliary observation device 320 to the first rotation axis unit 210. The configuration and function of the lens barrel unit 321, the attachment mechanism unit 323, the connecting unit 325, and the securing member 327 are similar to the configuration and function of these members in the auxiliary observation device 310 according to the first embodiment, and thus detailed description will be reduced or omitted herein. However, the circular arc shape of the attachment mechanism unit 323 is formed into a shape corresponding to the outer circumference of the housing 211 of the first rotation axis unit 210.

Herein, in the first embodiment, the auxiliary observation device 310 is attached to the barrel unit 112 of the microscope unit 110. As described in (1-1. Overall configuration of microscope device) above, the barrel unit 112 may be a section that is gripped by the surgeon when the surgeon moves the microscope unit 110 with a direct operation. Consequently, in the case of attempting to move the microscope unit 110 after attaching the auxiliary observation device 310, there is a possibility of the auxiliary observation device 310 becoming an impediment to an operation by the surgeon.

On the other hand, according to the second embodiment, the auxiliary observation device 320 is attached not to the barrel unit 112, but to the housing 211 constituting the first rotation axis unit 210. Consequently, after attaching the auxiliary observation device 320, in a case in which the surgeon attempts to move the microscope unit 110 with a direct operation, the auxiliary observation device 320 does not become an impediment to the operation by the surgeon, and operability for the surgeon can be improved further.

Additionally, since the auxiliary observation device 320 is attached to the rotating unit 212 of the housing 211, it is possible to rotate the auxiliary observation device 320 about the first axis $O_1$ together with the microscope unit 110, similarly to so the first embodiment. Consequently, the observation range provided by the auxiliary observation device 320 can be adjusted easily by rotating the auxiliary observation device 320.

The above thus describes a configuration of the auxiliary observation device 320 according to the second embodiment with reference to FIG. 5. According the auxiliary observation device 320, in addition to advantageous effects similar to those of the auxiliary observation device 310 according to the first embodiment, the following advantageous effects can be obtained.

Namely, the auxiliary observation device 320 is attached to the housing 211 of the first rotation axis unit 210, which is a not a section that is gripped by the surgeon when the surgeon attempts to move the microscope unit 110 with a direct operation. Consequently, even in the case in which the auxiliary observation device 320 has been attached, the auxiliary observation device 320 does not become an impediment to a direct operation, and the surgeon is able to grip the barrel unit 112 to move the microscope unit 110 like normal. Thus, operability for the surgeon can be improved. In this way, according to the second embodiment, there may be provided an auxiliary observation device 320 capable of further improving operability for the surgeon.

3. Third Embodiment

A third embodiment of the present disclosure will now be described. Note that the third embodiment corresponds to a modification of the configuration of attachment mechanism unit of the auxiliary observation device and of the attachment position of the auxiliary observation device with respect to the first embodiment described above, and other features (such as the configuration of the microscope system 1 and the overall configuration of the microscope device 10, for example) are similar to the first embodiment. Consequently, in the following description of the third embodiment, the features that differ from the first embodiment will be described primarily, whereas detailed description of features that overlap with the so first embodiment will be reduced or omitted.

(3-1. Configuration of Auxiliary Observation Device)

Figure 6:
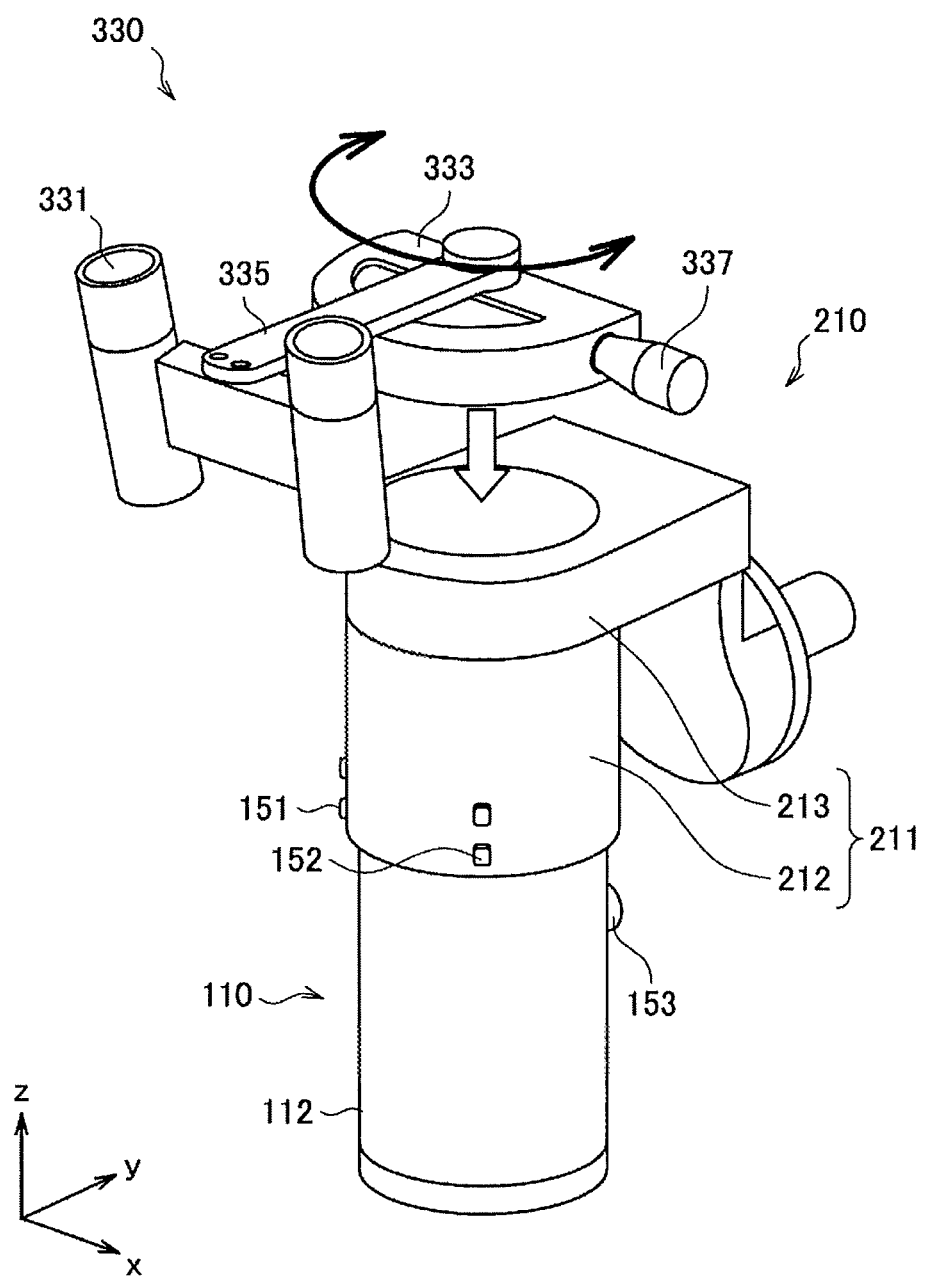
FIG. 6 is a diagram illustrating a method of attaching an auxiliary observation device according to a third embodiment to a first rotation axis unit.
Figure 7:
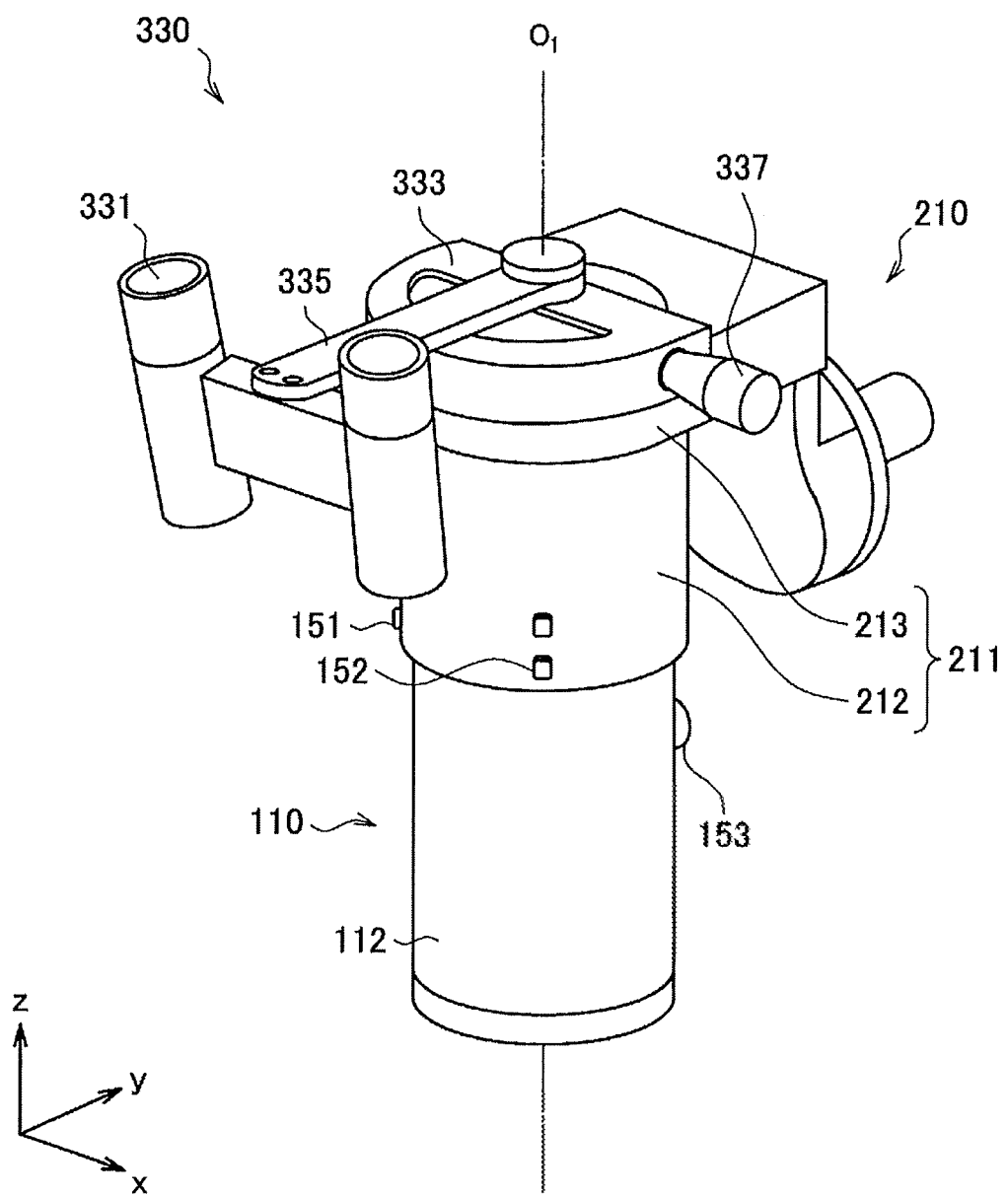
FIG. 7 is a profile diagram illustrating how an auxiliary observation device according to a third embodiment is attached to a first rotation axis unit.
Figure 8:
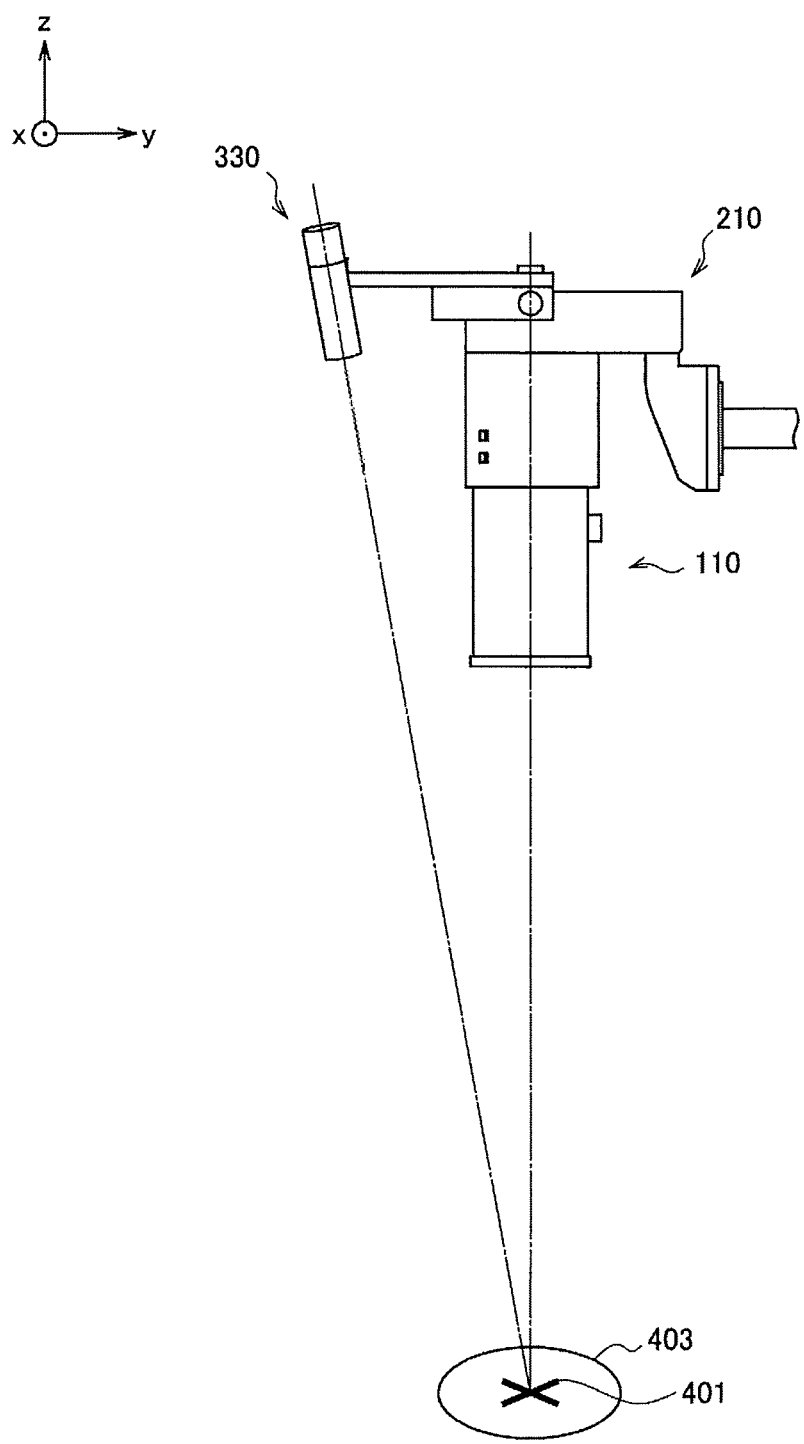
FIG. 8 is a profile diagram illustrating how an auxiliary observation device according to a third embodiment is attached to a first rotation axis unit.

A configuration of an auxiliary observation device according to the third embodiment will be described with reference to FIGS. 6 to 8. FIG. 6 is a diagram illustrating a method of attaching an auxiliary observation device according to the third embodiment to the first rotation axis unit 210. FIG. 7 is a perspective diagram illustrating how an auxiliary observation device according to the third embodiment is attached to the first rotation axis unit 210. FIG. 8 is a profile diagram illustrating how an auxiliary observation device according to the third embodiment is attached to the first rotation axis unit 210.

Note that similarly to FIGS. 3 and 4, FIGS. 6 to 8 illustrate an extraction of only the microscope unit 110 and the first rotation axis unit 210 from the microscope device 10 illustrated in FIG. 1. Since the configuration of the microscope unit 110 and the first rotation axis unit 210 is similar to that which is described in the above (1-2. Configuration of auxiliary observation device) with reference to FIGS. 3 and 4, detailed description will be reduced or omitted herein. Also, similarly to FIG. 4, FIG. 8 illustrates the observation target 401 as well as the irradiated range 403 irradiated by illuminating light from the microscope unit 110.

Referring to FIGS. 6 and 7, the auxiliary observation device 330 according to the third embodiment is made up of a lens barrel unit 331, an attachment mechanism unit 333, a connecting unit 335 that connects the lens barrel unit 331 and the attachment mechanism unit 333, and a securing member 337 for securing the auxiliary observation device 330 to the first rotation axis unit 210. The configuration and function of the lens barrel unit 331, the connecting unit 335, and the securing member 337 are similar to the configuration and function of these members in the auxiliary observation device 310 according to the first embodiment, and thus detailed description will be reduced or omitted herein. However, a rotation mechanism described later is provided at the site of connection between the connecting unit 335 and the attachment mechanism unit 333.

In the third embodiment, the configuration of the attachment mechanism unit 333 is different from the first embodiment. The attachment mechanism unit 333 is a mechanism for attaching the auxiliary observation device 330 to the first rotation axis unit 210. The attachment mechanism unit 333 includes a first section with an approximately semicircular shape corresponding to the shape of the top face of the housing 211 of the first rotation axis unit 210, and a second section extending a certain length in an approximately vertical direction from the rim of the circular arc shape of the first section.

When the auxiliary observation device 330 is attached to the first rotation axis unit 210, the auxiliary observation device 330 is mounted onto the first rotation axis unit 210 so that the first section of the attachment mechanism unit 333 is placed on the top face of the housing 211 of the first rotation axis unit 210, while the second section of the attachment mechanism unit 333 covers a region of a certain distance from the top face on the side face of the housing 211. At this point, the upper part of the housing 211 is the fixed unit 213 that rotatably supports the microscope unit 110 and the rotating unit 212. In this way, in the third embodiment, the auxiliary observation device 330 is attached to the fixed unit 213 of the first rotation axis unit 210.

Herein, in the first embodiment, the auxiliary observation device 310 is attached to the barrel unit 112 of the microscope unit 110. Also, in the second embodiment, the auxiliary observation device 320 is attached to the rotating unit 212 of the first rotation axis unit 210. As illustrated in FIGS. 4 and 5, with these configurations, the top end of the lens barrel unit 311 or 321 of the auxiliary observation device 310 or 320 (that is, the eyepiece) may be positioned immediately beside the microscope unit 110 and the first rotation axis unit 210. Consequently, when the surgeon peers into the lens barrel unit 311 or 312, there is a risk of the microscope unit 110 and the first rotation axis unit 210 interfering with the surgeon's head, and impairing the user experience for the surgeon.

On the other hand, according to the third embodiment, the auxiliary observation device 330 is attached to the top face of the housing 211 of the first rotation axis unit 210 (that is, the top face of the fixed unit 213). Consequently, as illustrated in FIG. 8, the eyepiece of the lens barrel unit 331 of the auxiliary observation device 330 may be positioned at a higher position than the microscope unit 110 and the first rotation axis unit 210. Thus, when the surgeon peers into the lens barrel unit 331, the microscope unit 110 and the first rotation axis unit 210 do not become an impediment to the surgeon, and the user experience for the surgeon can be improved further.

Herein, in the auxiliary observation device 330, a rotation mechanism is provided at the site of connection between the connecting unit 335 and the attachment mechanism unit 333, thereby allowing the lens barrel unit 331 and the connecting unit 335 to rotate with respect to the attachment mechanism unit 333. As illustrated in FIG. 6, for example, the rotation mechanism is realized by providing openings that penetrate through the connecting unit 335 and the attachment mechanism unit 333, and inserting a connecting member such as a bolt through these openings. In this case, the rotation mechanism may be configured so that the rotation axis of the lens barrel unit 331 and the connecting unit 335 is approximately coaxial with the rotation axis in the first rotation axis unit 210 (first axis $O_1$). In other words, in the auxiliary observation device 330, the lens barrel unit 331 may be configured to be rotatable about the first axis $O_1$.

As described above, since the auxiliary observation device 330 is attached to the fixed unit 213 of the first rotation axis unit 210, the auxiliary observation device 330 is unable to rotate together with the microscope unit 110 like the auxiliary observation devices 310 and 320 according to the first and second embodiments. However, by providing a rotation mechanism as above, it becomes possible for the lens barrel unit 331 to rotate about the first axis $O_1$ with respect to the attachment so mechanism unit 333, or in other words, with respect to the fixed unit 213 of the first rotation axis unit 210. Consequently, the observation range provided by the auxiliary observation device 330 can be adjusted easily by rotating the auxiliary observation device 330, similarly to the first and second embodiments.

The above thus describes a configuration of the auxiliary observation device 330 according to the third embodiment with reference to FIGS. 6 to 8. According the auxiliary observation device 330, in addition to advantageous effects similar to those of the auxiliary observation device 310 according to the first embodiment, the following advantageous effects can be obtained.

Namely, the auxiliary observation device 330 is attached to the top face of the housing 211 of the first rotation axis unit 210. Consequently, the eyepiece of the lens barrel unit 331 of the auxiliary observation device 330 becomes arranged at a higher position than the microscope unit 110 and the first rotation axis unit 210, and when the surgeon peers into the lens barrel unit 331, the microscope unit 110 and the first rotation axis unit 210 do not become an impediment to the surgeon. In this way, according to the third embodiment, there may be provided an auxiliary observation device 330 capable of further improving the user experience for the surgeon.

4. Fourth Embodiment

A fourth embodiment of the present disclosure will now be described. Note that the fourth embodiment corresponds to providing an angle adjustment mechanism described later on the lens barrel unit 311, 321, or 331 of the auxiliary observation device 310, 320, or 330 according to the first to third embodiments 26 described above. Other features (such as the configuration of the microscope system 1 and the overall configuration of the microscope device 10, for example) are similar to the first to third embodiments. Consequently, in the following description of the fourth embodiment, the features that differ from the first to third embodiments will be described primarily, whereas detailed description of features that overlap with the first to third embodiments will be reduced or omitted.

Note that in the following description of the fourth embodiment, a configuration in which an angle adjustment mechanism is provided on the lens barrel unit 331 of the auxiliary observation device 330 according to the third embodiment is described as an example. However, the fourth embodiment is not limited to such an example, and an auxiliary observation device according to the fourth embodiment may also be configured by providing an angle adjustment mechanism on the lens barrel unit 311 or 321 of the auxiliary observation device 310 or 320 according to the first and second embodiments.

(4-1. Configuration of Auxiliary Observation Device)

Figure 9:
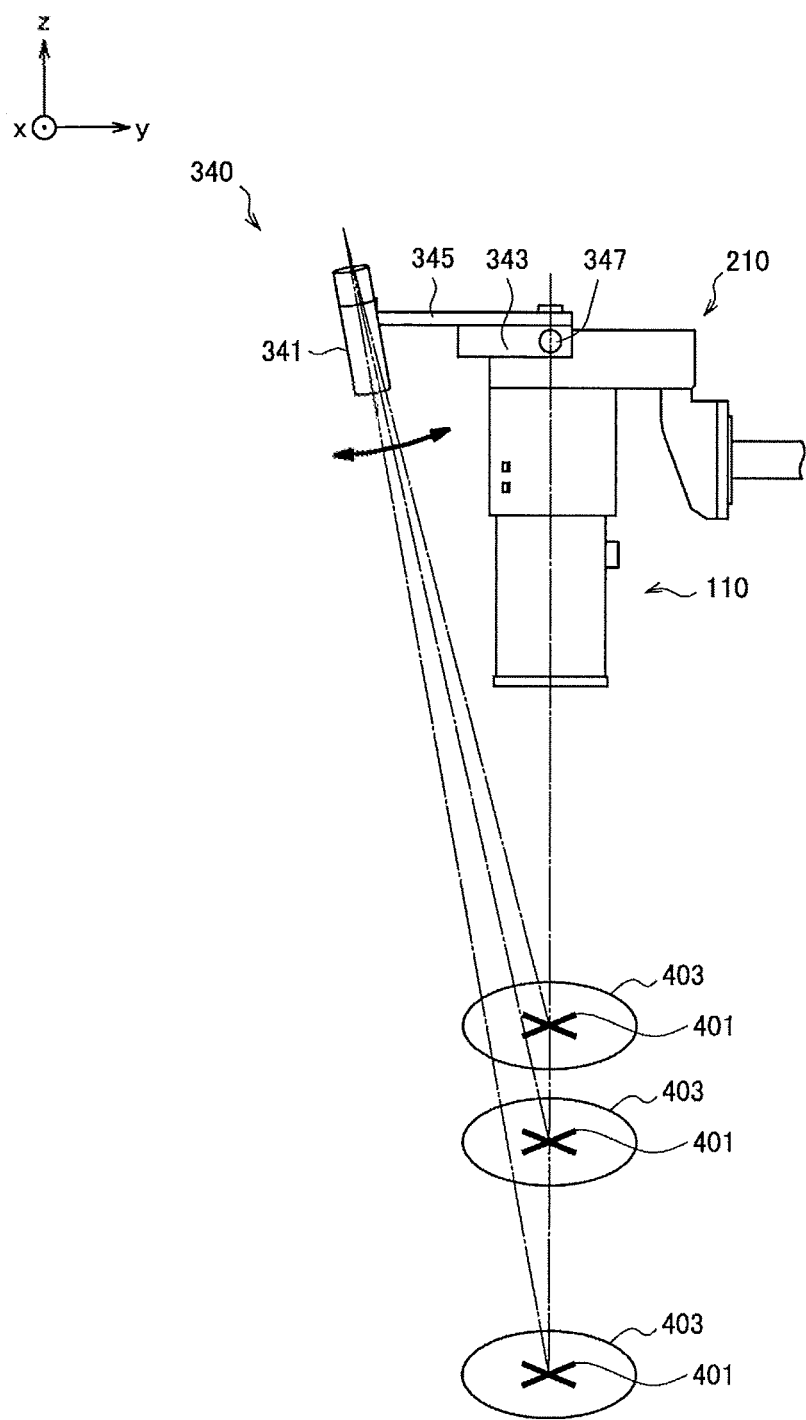
FIG. 9 is a profile diagram illustrating how an auxiliary observation device according to a fourth embodiment is attached to a first rotation axis unit.

A configuration of an auxiliary observation device according to the fourth embodiment will be described with reference to FIG. 9. FIG. 9 is a profile diagram illustrating how an auxiliary observation device according to the fourth embodiment is attached to the first rotation axis unit 210. Note that similarly to FIGS. 6 to 8, FIG. 9 illustrates an extraction of only the microscope unit 110 and the first rotation axis unit 210 from the microscope device 10 illustrated in FIG. 1. Since the configuration of the microscope unit 110 and the first rotation axis unit 210 is similar to that which is described in the above (1-2. Configuration of auxiliary observation device) with reference to FIGS. 3 and 4, detailed description will be reduced or omitted herein. Also, similarly to FIG. 8, FIG. 9 illustrates the observation target 401 as well as the irradiated range 403 irradiated by illuminating light from the microscope unit 110.

Referring to FIG. 9, the auxiliary observation device 340 according to the third embodiment is made up of a lens barrel unit 341, an attachment mechanism unit 343, a connecting unit 345 that connects the lens barrel unit 341 and the attachment mechanism unit 343, and a securing member 347 for securing the auxiliary observation device 340 to the first rotation axis unit 210. Herein, the configuration and function of the respective component members of the auxiliary observation device 340, namely, the lens barrel unit 341, the attachment mechanism unit 343, the connecting unit 345, and the securing member 347 are similar to the configuration and function of these members in the auxiliary observation device 330 according to the third embodiment, and thus detailed description will be reduced or omitted herein.

However, in the fourth embodiment, there is provided, at the site of connection between the lens barrel unit 341 and the connecting unit 345, an angle adjustment mechanism enabling adjustment of the connection angle of the lens barrel unit 341 with respect to the connecting unit 345, or in other words, the tilt angle with respect to the optical axis of the microscope unit 110. In other words, the auxiliary observation device 340 is configured to enable adjustment of the tilt angle of the lens barrel unit 341 with respect to the optical axis of the microscope unit 110. With such an angle adjustment mechanism, as illustrated in FIG. 9, it becomes possible to adjust the direction of the optical axis of the lens barrel unit 341, or in other words, the direction of observation provided by the lens barrel unit 341.

Herein, when observing the operating site using the microscope unit 110 during surgery, it is anticipated that the operating site will be observed from a variety of distances and angles while appropriately modifying factors such as the focal length and the magnification of the microscope unit 110. Consequently when the picture of the operating site is no longer displayed normally and the auxiliary observation device 340 is attached to the microscope unit 110, the distance between the microscope unit 110 and the operating site is not necessarily always going to be the same.

FIG. 9 illustrates how, by the angle adjustment mechanism, the direction of the optical axis of the lens barrel unit 341 is adjusted to point towards the observation target 401 in accordance with the distance between the microscope unit 110 and the observation target 401. In this way, by appropriately adjusting the direction of the optical axis of the lens barrel unit 341 in accordance with the distance between the microscope unit 110 and the observation target 401, it becomes possible to observe a clearer picture of the observation target 401 with the lens barrel unit 341.

Note that the optical system provided inside the lens barrel unit 341 may also be provided with a magnification adjustment function and/or a focal length adjustment function. By providing a magnification adjustment function and/or a focal length adjustment function, in the case of adjusting the angle of the lens barrel unit 341, the magnification and/or the focal length of the lens barrel unit 341 can be adjusted appropriately in accordance with the distance between the lens barrel unit 341 and the observation target 401, making it possible to observe an even clearer picture of the observation target 401.

The above thus describes a configuration of the auxiliary observation device 340 according to the fourth embodiment with reference to FIG. 9. According the auxiliary observation device 340, in addition to advantageous effects similar to those of the auxiliary observation device 330 according to the third embodiment, the following advantageous effects can be obtained.

In other words, in the auxiliary observation device 340, there is provided an angle adjustment mechanism enabling adjustment of the tilt angle of the lens barrel unit 341 with respect to the optical axis of the microscope unit 110. Consequently, with such an angle adjustment mechanism, by appropriately adjusting the direction of the optical axis of the lens barrel unit 341 in accordance with the distance between the microscope unit 110 and the observation target 401, it becomes possible to observe a clearer picture of the observation target 401 with the lens barrel unit 341.

5. Supplemental Remarks

The preferred embodiment(s) of the present disclosure has/have been described above with reference to the accompanying drawings, whilst the present disclosure is not limited to the above examples. A person skilled in the an may find various alterations and modifications within the scope of the appended claims, and it should be understood that they will naturally come under the technical scope of the so present disclosure.

For example, the features described in the first to fourth embodiments above may also be combined with each other where possible. For example, the magnification adjustment function and/or the focal length adjustment function described in the fourth embodiment may also be provided in the optical system of the lens barrel unit 311, 321, or 331 or the auxiliary observation device 310, 320, or 330 according to the first to third embodiments.

Additionally, the storage location of the auxiliary observation device 320, 330, or 340 according to the second to fourth embodiments may also be similar to the first embodiment. In other words, the storage location of the auxiliary observation device 320, 330, or 340 is not particularly limited, and the auxiliary observation device 320, 330, or 340 may also be stored together with a manual in the dedicated storage unit 133 provided in the microscope device 10, or in an arbitrary location that is easily retrievable during an emergency, such as inside the operating room, for example.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A surgical microscope device, including: a microscope unit that images an observation target, and outputs a picture signal; a support unit that supports the microscope unit, and is configured as a balance arm; and an auxiliary observation device that is attachable to the microscope unit or the support unit, and is configured to enable observation of an observation range provided by the microscope unit.

(2)

The surgical microscope device according to (1), in which the support unit rotatably supports the microscope unit about a first rotation axis approximately parallel to an optical axis of the microscope unit, and the auxiliary observation device is attached to the microscope unit and enables rotation about the first rotation axis together with the microscope unit.

(3)

The surgical microscope device according to (1) or (2), in which the auxiliary observation device is attached to a section other than a section gripped by a surgeon, the section being provided on the microscope unit.

(4)

The surgical microscope device according to (1), in which the microscope unit has a barrel unit provided with an objective lens on a bottom end, the support unit supports the microscope unit on a top end of the barrel unit, and the auxiliary observation device is attached to a top face of a section of the support unit that supports the microscope unit.

(5)

The surgical microscope device according to any one of (1) to (4), in which the auxiliary observation device includes a lens barrel unit internally provided with an optical system for performing enlarged observation of the observation target, and an attachment mechanism unit for attaching the auxiliary observation device to the microscope unit or the support unit, and the lens barrel unit is configured to enable rotation about a first rotation axis approximately parallel to an optical axis of the microscope unit.

(6) The surgical microscope device according to any one of (1) to (5), in which the auxiliary observation device includes a lens barrel unit internally provided with an optical system for performing enlarged observation of the observation target, and an attachment mechanism unit for attaching the auxiliary observation device to the microscope unit or the support unit, and the lens barrel unit is configured to enable adjustment of a tilt angle with respect to an optical axis of the microscope unit.

(7) The surgical microscope device according to any one of (1) to (6), in which an optical system provided in the auxiliary observation device is configured to enable adjustment of at least one of a magnification and a focal length.

(8) The surgical microscope device according to any one of (1) to (7), in which the surgical microscope unit includes a storage unit for storing the auxiliary observation device.

(9) A surgical microscope system, including: a microscope device, including a microscope unit that images an observation target and outputs a picture signal, a support unit that supports the microscope unit and is configured as a balance arm, and an auxiliary observation device that is attachable to the microscope unit or the support unit, and is configured to enable observation of an observation range provided by the microscope unit; and a display device that displays a picture based on the picture signal.

REFERENCE SIGNS LIST 1 microscope system
10 microscope device
20 display device
110 microscope unit
120 support unit (arm unit)
130 base unit
131 platform
132 casters
133 storage unit
140 control device
210 first rotation axis unit
220 second rotation axis unit
230 third rotation axis unit
240 fourth rotation axis unit (parallelogram link mechanism)
250 fifth rotation axis unit
260 sixth rotation axis unit
241, 242, 243, 244 arm
245, 246, 247, 248 joint unit
271 first arm unit
272 second arm unit
273 third arm unit
274 fourth arm unit
310, 320, 330, 340 auxiliary observation device
311, 321, 331, 341 lens barrel unit
313, 323, 333, 343 attachment mechanism unit
315, 325, 335, 345 connecting unit
317, 327, 337, 347 securing member

The invention claimed is:

1. A surgical microscope device, comprising:
   a microscope that images an observation target, and outputs an image signal;
   a controller that enables a display of an image on a display device of the observation target based on the image signal outputted from the microscope;
   a support arm that supports the microscope, and is configured as a balance arm; and
   an auxiliary observation device that is separable from and attachable to the microscope or the support arm, and is configured to enable observation of an observation range provided by the microscope when an abnormality occurs and the image of the observation target is not displayed normally on the display device,
   wherein the support arm rotatably supports the microscope about a first rotation axis at a first joint and the first rotation axis is aligned with an optical axis of the microscope,
   the auxiliary observation device is enabled to rotate about the first rotation axis,
   the auxiliary observation device includes an attachment mechanism that positions an eyepiece of the auxiliary observation device higher than the microscope and the first joint and the attachment mechanism prevents the eyepiece of the auxiliary observation device from being positioned lower than the microscope and the first joint.

2. The surgical microscope device according to claim 1, wherein
   the auxiliary observation device is attached to a section other than a section gripped by a surgeon, the section being provided on the microscope.

3. The surgical microscope device according to claim 1, wherein
   the microscope has a barrel provided with an objective lens on a bottom end,
   the support arm supports the microscope on a top end of the barrel, and
   the auxiliary observation device is attached to a top face of a section of the support arm that supports the microscope.

4. The surgical microscope device according to claim 3, wherein
   the auxiliary observation device includes a lens barrel internally provided with an optical system for performing enlarged observation of the observation target, and an attachment mechanism for attaching the auxiliary observation device to the microscope or the support arm, and
   the lens barrel is configured to enable rotation about the first rotation axis approximately parallel to an optical axis of the microscope.

5. The surgical microscope device according to claim 1, wherein
   the auxiliary observation device includes a lens barrel internally provided with an optical system for performing enlarged observation of the observation target, and an attachment mechanism for attaching the auxiliary observation device to the microscope or the support arm, and
   the lens barrel is configured to enable adjustment of a tilt angle with respect to an optical axis of the microscope.

6. The surgical microscope device according to claim 1, wherein
   an optical system provided in the auxiliary observation device is configured to enable adjustment of at least one of a magnification and a focal length.

7. The surgical microscope device according to claim 1, wherein
   the surgical microscope device includes a storage unit for storing the auxiliary observation device.

8. The surgical microscope device according to claim 1, wherein:
the auxiliary observation device is enabled to rotate about the optical axis of the microscope.

9. The surgical microscope device according to claim 1, wherein:
the microscope has a cylindrically shaped barrel;
a bottom end of the cylindrically shaped barrel includes an objective lens; and
a top end of the cylindrically shaped barrel is attached to the first joint.

10. The surgical microscope device according to claim 9, wherein the optical axis of the microscope is along a center of the cylindrically shaped barrel.

11. The surgical microscope device according to claim 1, wherein:
the attachment mechanism attaches the auxiliary observation device to a top surface of the support arm, and
the attachment mechanism includes an auxiliary joint configured to rotate the auxiliary observation device about the first rotation axis.

12. The surgical microscope device according to claim 1, wherein:
the auxiliary observation device is attached to the microscope, and
the auxiliary observation device is enabled to rotate about the first rotation axis together with the microscope.

13. The surgical microscope device according to claim 1, wherein the auxiliary observation device further includes a connecting unit that connects the eyepiece of the auxiliary observation device to the attachment mechanism, a longest dimension of the connecting unit being configured to rotate about the first rotation axis only within a plane that is perpendicular to the optical axis of the microscope.

14. A surgical microscope system, comprising:
a microscope device, including a microscope that images an observation target and outputs an image signal;
a display device;
a controller that enables a display of an image on the display device of the observation target based on the image signal outputted from the microscope device;
a support arm that supports the microscope and is configured as a balance arm; and
an auxiliary observation device that is separable from and attachable to the microscope or the support arm, and is configured to enable observation of an observation range provided by the microscope when an abnormality occurs and the image of the observation target is not displayed normally on the display device,
wherein the support arm rotatably supports the microscope about a first rotation axis at a first joint and the first rotation axis is aligned with an optical axis of the microscope,
the auxiliary observation device is enabled to rotate about the first rotation axis, and
the auxiliary observation device includes an attachment mechanism that positions an eyepiece of the auxiliary observation device higher than the microscope and the first joint and the attachment mechanism prevents the eyepiece of the auxiliary observation device from being positioned lower than the microscope and the first joint.

* * * * *